United States Patent
McConnell et al.

(10) Patent No.: US 10,545,157 B2
(45) Date of Patent: Jan. 28, 2020

(54) KIDNEY DISEASE BIOMARKER

(71) Applicant: Randox Teoranta, Dungloe (IE)

(72) Inventors: Ivan McConnell, Antrim (GB); Ciaran Richardson, Dungloe (IE); John Lamont, Antrim (GB); Stephen Peter Fitzgerald, Antrim (GB)

(73) Assignee: Randox Laboratories Ltd., Northern Ireland (GB)

( * ) Notice: Subject to any disclaimer, the term of this patent is extended or adjusted under 35 U.S.C. 154(b) by 409 days.

(21) Appl. No.: 15/026,577

(22) PCT Filed: Oct. 6, 2014

(86) PCT No.: PCT/EP2014/071354
§ 371 (c)(1),
(2) Date: Mar. 31, 2016

(87) PCT Pub. No.: WO2015/049390
PCT Pub. Date: Apr. 9, 2015

(65) Prior Publication Data
US 2016/0216278 A1   Jul. 28, 2016

(30) Foreign Application Priority Data

Oct. 4, 2013 (GB) .................................. 1317621.9

(51) Int. Cl.
*G01N 31/00* (2006.01)
*G01N 33/53* (2006.01)
*G01N 33/68* (2006.01)

(52) U.S. Cl.
CPC . *G01N 33/6893* (2013.01); *G01N 2333/4716* (2013.01); *G01N 2333/523* (2013.01); *G01N 2800/347* (2013.01); *G01N 2800/52* (2013.01); *G01N 2800/60* (2013.01)

(58) Field of Classification Search
None
See application file for complete search history.

(56) References Cited

FOREIGN PATENT DOCUMENTS

WO    2006034032 A2    3/2006

OTHER PUBLICATIONS

Tockman et al. (Cancer Research 52:2711s-2718s, 1992).*
Tascilar et al. (Annals of Oncology 10,Suppl. 4:S107-S110, 1999).*
Moreno De Vega, C., International Search Report and Written Opinion, PCT/EP2014/071354, dated Jul. 14, 2015.
Kamijo et al., "Urinary fatty acid-binding protein as a new clinical marker of the progression of chronic renal disease", Journal of Laboratory and Clinical Medicine, vol. 143, No. 1, Jan. 1, 2004, pp. 23-30.
Ozata, M. et al., "Increased Fasting Plasma Acylation-Stimulating Protein Concentrations in Nephrotic Syndrome," Journal of Clinical Endocrinology and Metabolism, vol. 87, No. 2, Feb. 1, 2002, pp. 853-858.
Tang et al., "Increased plasma acylation-stimulating protein in pediatric proteinuric renal disease", Pediatr. Nephrol., vol. 23, 2008, pp. 959-964.

* cited by examiner

*Primary Examiner* — Lisa V Cook
(74) *Attorney, Agent, or Firm* — Gavrilovich, Dodd & Lindsey LLP

(57) ABSTRACT

The disclosure provides methods and solid states devices for detecting and staging chronic kidney disease in a patient, where the levels of biomarkers in a sample obtained from a patient are elevated or reduced compared to the levels in a sample obtained from healthy subject. In addition, the disclosure provides the use of methods and solid state devices for measurement of specific biological markers for determining the efficacy of a treatment for chronic kidney disease and for determining a drug treatment protocol for a subject suffering from chronic kidney disease.

11 Claims, 11 Drawing Sheets

KIDNEY DISEASE BIOMARKER

CROSS REFERENCE TO RELATED APPLICATIONS

This application is a U.S. National Stage Application filed under 35 U.S.C. § 371, and claims priority International Application No. PCT/EP2014/071354, filed Oct. 6, 2014, which application claims priority to Great Britain Application No. 1317621.9, filed Oct. 4, 2013, the disclosures of which are incorporated herein by reference in their entirety.

FIELD OF THE INVENTION

The present invention relates to kidney disease and methods for its diagnosis.

BACKGROUND OF THE INVENTION

Kidney disease is a general term, which describes a class of conditions in which the kidneys fail to filter and remove waste products from the blood. There are two forms of kidney disease; acute kidney injury (AKI) and chronic kidney disease (CKD). CKD is usually asymptomatic, except in its most advanced state. Consequently, blood and/or urine tests generally are required to make a diagnosis.

The definition of CKD developed by the Kidney Disease Outcomes Quality Initiative (KDOQI) was:
1. Kidney damage present for at least 3 months, as defined by structural or functional abnormalities (most often based on increased albuminuria e.g. urinary albumin/creatinine ratio [UACR]≥30 mg/g) and/or
2. Glomerular filtration rate (GFR)<60 mL/min/1.73 m$^2$ present for at least 3 months.

Within this framework, KDOQI then classified CKD into five stages, as follows:
Stage 1: Kidney damage with GFR≥90 mL/min/1.73 m$^2$.
Stage 2: Kidney damage with GFR 60-89 mL/min/1.73 m$^2$.
Stage 3: GFR 30-59 mL/min/1.73 m$^2$.
Stage 4: GFR 15-29 mL/min/1.73 m$^2$.
Stage 5: GFR<15 mL/min/1.73 m$^2$ or kidney failure treated by dialysis or transplantation.

In the United States, based on data from the 1999-2006 National Health and Nutrition Examination Survey (NHANES) study, an estimated 11.1 percent (22.4 million) of adults aged 20 or older have CKD stages 1-3. An additional 0.8 million U.S. adults aged 20 or older have CKD stage 4, and more than 0.3 million have stage 5 CKD and receive hemodialysis.

Analyses of NHANES data between 1988-1994 and 1999-2004 suggest that the prevalence of CKD is rising for every CKD stage, but with a particular increase in the prevalence of individuals classified with CKD stage 3. The number of patients with stage 5 CKD requiring dialysis also has increased. It has been estimated that more than 700,000 individuals will have End Stage Renal Disease (ESRD) by 2015.

Although CKD can be caused by primary kidney disease (e.g. glomerular diseases, tubulointerstitial diseases, obstruction, and polycystic kidney disease), in the vast majority of patients with CKD, the kidney damage is associated with other medical conditions such as diabetes and hypertension. In 2008, excluding those with ESRD, 48 percent of Medicare patients with CKD had diabetes, 91 percent had hypertension, and 46 percent had atherosclerotic heart disease. Other risk factors for CKD include age, obesity, family history, and ethnicity.

CKD has been associated with numerous adverse health outcomes. Many studies have reported that a GFR of 30-59 mL/min/1.73 m$^2$ is associated with an increased risk of mortality, cardiovascular disease, fractures, bone loss, infections, cognitive impairment, and frailty. Similarly, there appears to be a graded relationship between the severity of proteinuria or albuminuria and adverse health outcomes, including mortality, ESRD, and cardiovascular disease. Further, the risk for adverse outcomes conferred by reduced GFR and increased albuminuria (or proteinuria) appears to be independent and multiplicative.

The rationale for considering screening for early-stage CKD includes the high and rising prevalence of CKD, its known risk factors, its numerous adverse health consequences, its long asymptomatic phase, the availability of potential screening tests for CKD, and the availability of treatments that may alter the course of early-stage CKD and reduce complications of early-stage CKD or its associated health conditions.

Some organizations already recommend CKD screening in selected populations. Kidney Disease: Improving Global Outcomes (KDIGO) recommends screening of all patients with hypertension, diabetes, or cardiovascular disease. The American Diabetes Association recommends annual screening of all adults with diabetes, based on "expert consensus or clinical experience." The Joint National Committee on Prevention, Detection, Evaluation, and Treatment of High Blood Pressure (JNC7) recommends annual screening of all patients with combined hypertension and diabetes. Also advocating selected screening, the National Kidney Foundation sponsors free CKD screening for all adults with hypertension, diabetes, or a primary relative with a history of kidney disease, hypertension, or diabetes.

In most patients with CKD stages 1 to 3 GFR declines slowly. However, the rate of decline varies among individuals, and many factors appear to impact progression. Because CKD stages 1 and 2 usually progress asymptomatically, detection of early-stage CKD requires laboratory testing.

Some organizations recommend monitoring for changes in kidney function or damage in patients with CKD. For example, the Kidney Disease Outcomes Quality Initiative (KDOQI) recommends at least annual estimated GFR measurement in adults with CKD in order to predict onset of ESRD and evaluate the effect of CKD treatments. JNC7 recommends annual quantitative measurement of albuminuria in all patients with "kidney disease." KDOQI also recommends more frequent monitoring of CKD patients with worsening kidney function.

Despite the importance of measuring clinical parameters for CKD in serum or urine, there are few diagnostic tests to detect early stage CKD and monitor the progression of this disease. Measurement of GFR is not sufficiently sensitive for early detection of kidney disease, while the measurement of urinary protein is not specific for kidney disease, nor is it suitable for monitoring the progression of the disease. Therefore, there is a requirement for a specific and sensitive clinical marker or combination of markers for the diagnosis of early CKD and staging of kidney disease.

SUMMARY OF THE INVENTION

The present invention provides methods for the diagnosis of kidney disease. More specifically the invention provides biomarkers which provide a means for an early diagnosis and staging of CKD.

The present invention is based on the surprising finding by the inventors that altered levels of individual biomarkers can be detected in serum from patients with stage 1, stage 2 and stage 3 CKD compared with serum from control individuals. Biomarkers which can be detected at altered levels in serum from patients with stage 1, stage 2 and stage 3 CKD compared with serum from control individuals include complement C3a(des)Arg (C3a desArg), interleukin 8 (IL-8), macrophage inflammatory protein 1 alpha (MIP 1α), adepnectin (ADPN), dipeptidyl peptidase 4 (CD26), Creatinine, c-reactive protein (CRP), cystatin c (CYSC), D-dimer, endothelial growth factor (EGF), e selectin (ESEL), fatty acid-binding protein 1 (liver fatty acid-binding protein; FABP1 or LFABP), granulocyte and macrophage colony stimulating factor (GMCSF), intercellular adhesion molecule 1 (ICAM1), interferon gamma (IFNγ), interleukin 10 (IL10), interleukin 15 (IL15), interleukin 1 alpha (IL1α), interleukin 1 beta (IL1β), interleukin 2 (IL2), interleukin 4 (IL4), interleukin 5 (IL5), interleukin 6 (IL6), l selectin (LSEL), monocyte chemotactic protein 1 (MCP1), matrix metalloproteinase 9 (MMP9), neutrophil gelatinase-associated lipocalin (NGAL), neuron specific enolase (NSE), p selectin (PSEL), soluble interleukin 2 alpha (sIL2α), soluble interleukin 6 receptor (sIL6R), soluble tumour necrosis factor receptor 1 (STNFR1), soluble tumour necrosis factor receptor 2 (STNFR2), tumour necrosis factor alpha (TNFα), vascular endothelial growth factor (VEGF) and vascular cell adhesion molecule 1 (VCAM1).

In a first aspect, the invention provides a method for detecting kidney disease in a subject, comprising measuring the amount of a biomarker in a sample obtained from the subject, and determining whether the amount of the biomarker is altered compared to a normal control, wherein the biomarker is selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1.

In a second aspect, the invention provides a solid state device comprising a substrate comprising an antibody that binds to a biomarker selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1.

In a third aspect, the invention provides a method of determining the efficacy of a treatment for chronic kidney disease, comprising measuring the amount of a biomarker in a sample obtained from a subject receiving such treatment, wherein the biomarker is selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1, and comparing the level of the biomarker to that of a sample from an untreated control to determine whether the treatment has had the effect of altering the biomarker level.

In a fourth aspect, the invention provides a method of determining the efficacy of a treatment for chronic kidney disease, comprising measuring the amount of a biomarker in a sample obtained from a subject receiving such treatment, wherein the biomarker is selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1, and comparing the level of the biomarker to that of a sample obtained from the subject before treatment, wherein a reduction or maintenance in the stage of chronic kidney disease or a slowing of progression through stages of chronic kidney disease following treatment indicates that the treatment has been successful.

In a fifth aspect, the invention provides a method of determining a drug treatment protocol for a subject suffering from chronic kidney disease, comprising, in a sample taken from a subject treated with the drug, comparing the level of a biomarker selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1 to the level in sample obtained from an untreated control to determine whether the drug has had the effect of altering the biomarker level, and selecting a drug treatment protocol based on whether the subject has stage 1, stage 2 or stage 3 chronic kidney disease.

In a sixth aspect, the invention provides the use of a kit for screening for kidney disease in a method according to any of the proceeding aspects of the invention, the kit comprising a probe that binds specifically to a biomarker selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF and VCAM1, or reagents for an immunoassay or 1D or 2D gel electrophoresis for detecting the level of a biomarker selected from the group consisting of C3a desArg, IL-8, MIP 1α, ADPN, CD26, Creatinine, CRP, CYSC, D-dimer, EGF, ESEL, GMCSF, ICAM1, IFNγ, IL10, IL15, IL1α, IL1β, IL2, IL4, IL5, IL6, FABP1, LSEL, MCP1, MMP9, NGAL, NSE, PSEL, sIL2α, sIL6R, STNFR1, STNFR2, TNFα, VEGF and VCAM1.

DESCRIPTION OF THE DRAWINGS

The invention is described with reference to the following Figures in which.

DETAILED DESCRIPTION OF THE INVENTION

Figure 1:
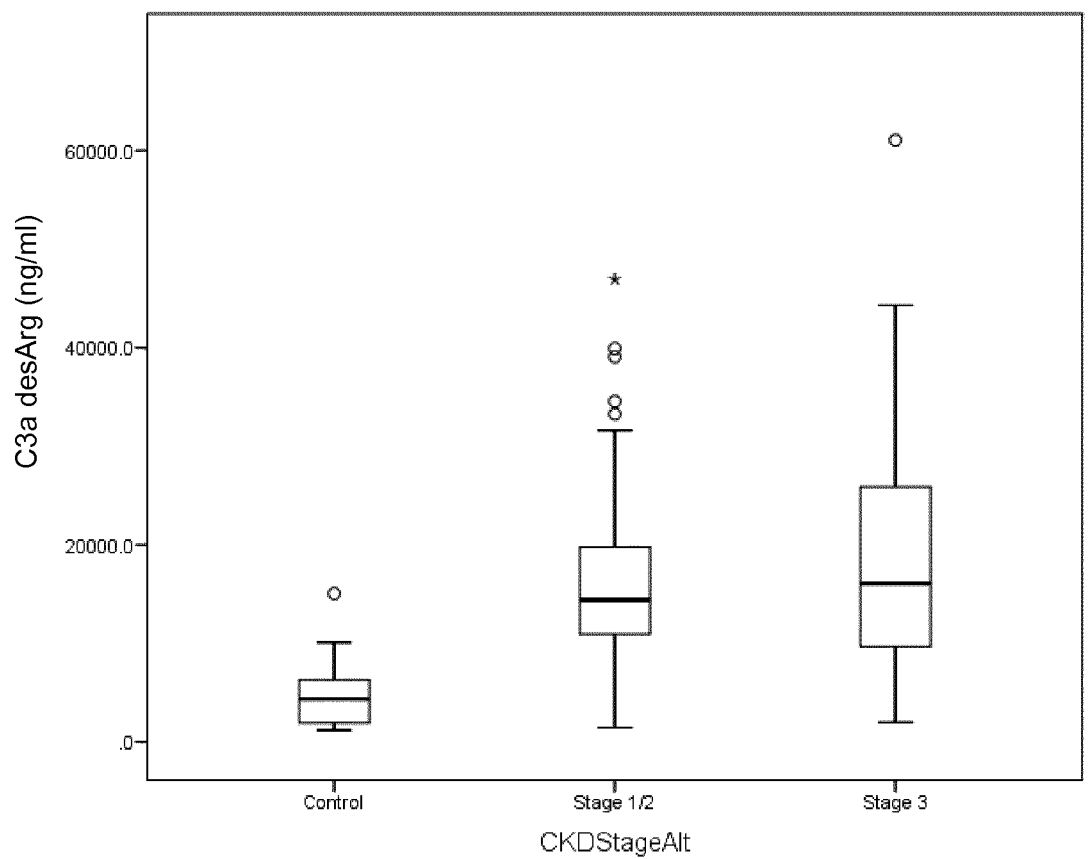
FIG. 1 shows boxplots that summarise the levels of C3a desArg measured in serum samples taken from Healthy controls, patients suffering from Stage 1 or Stage 2 CKD and patients suffering from Stage 3 CKD.
Figure 2:
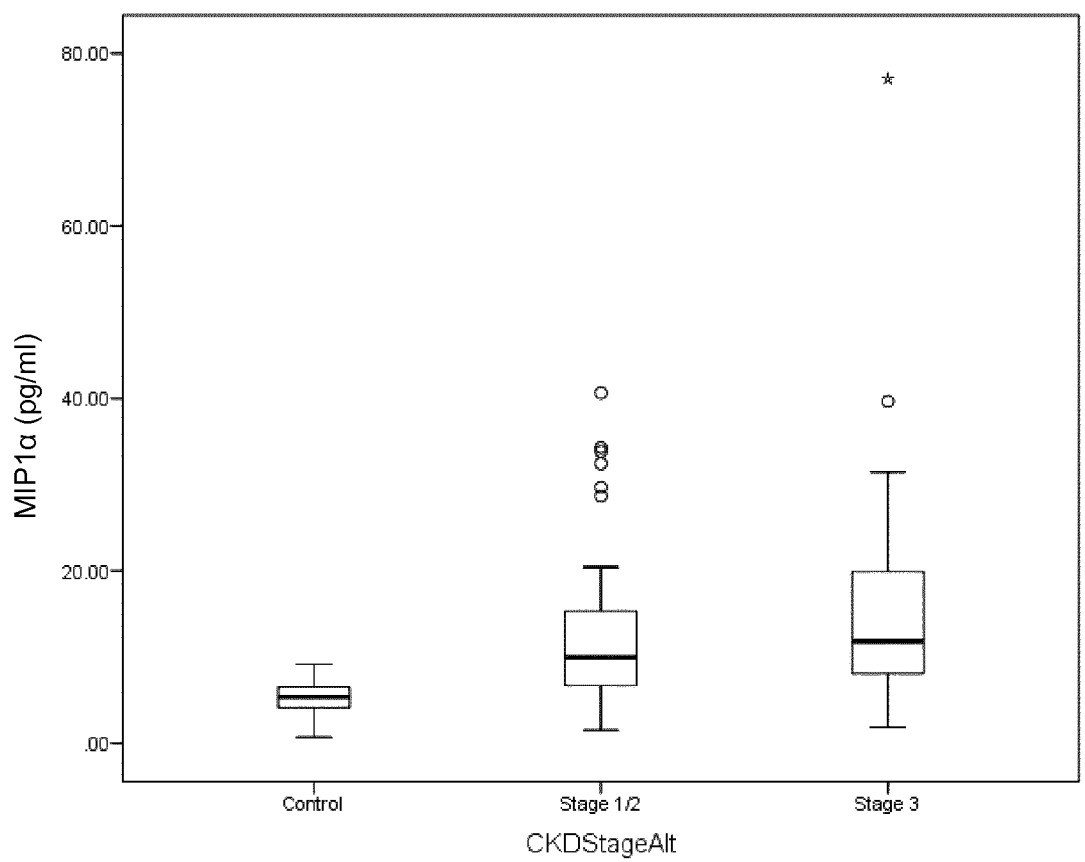
FIG. 2 shows boxplots that summarise the levels of MIP 1α, measured in serum samples taken from Healthy controls, patients suffering from Stage 1 or Stage 2 CKD and patients suffering from Stage 3 CKD.
Figure 3:
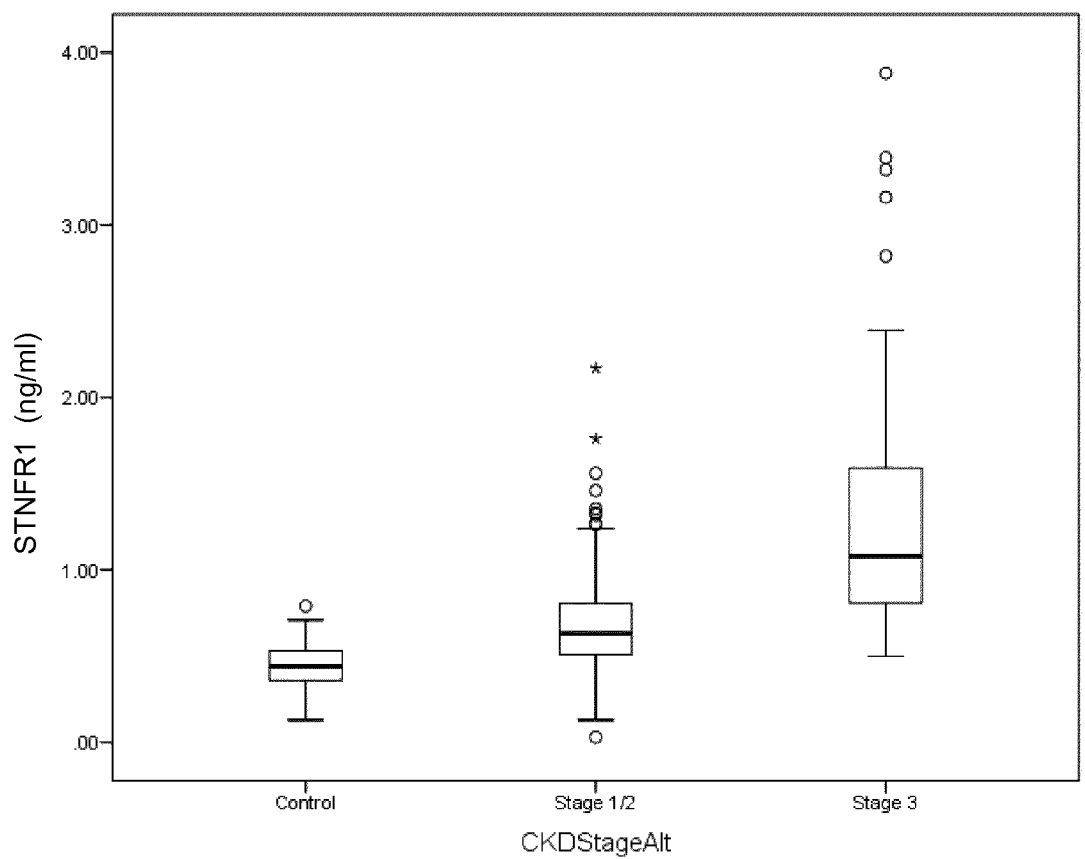
FIG. 3 shows boxplots that summarise the levels of STNFR1 measured in serum samples taken from Healthy controls, patients suffering from Stage 1 or Stage 2 CKD and patients suffering from Stage 3 CKD.
Figure 4:
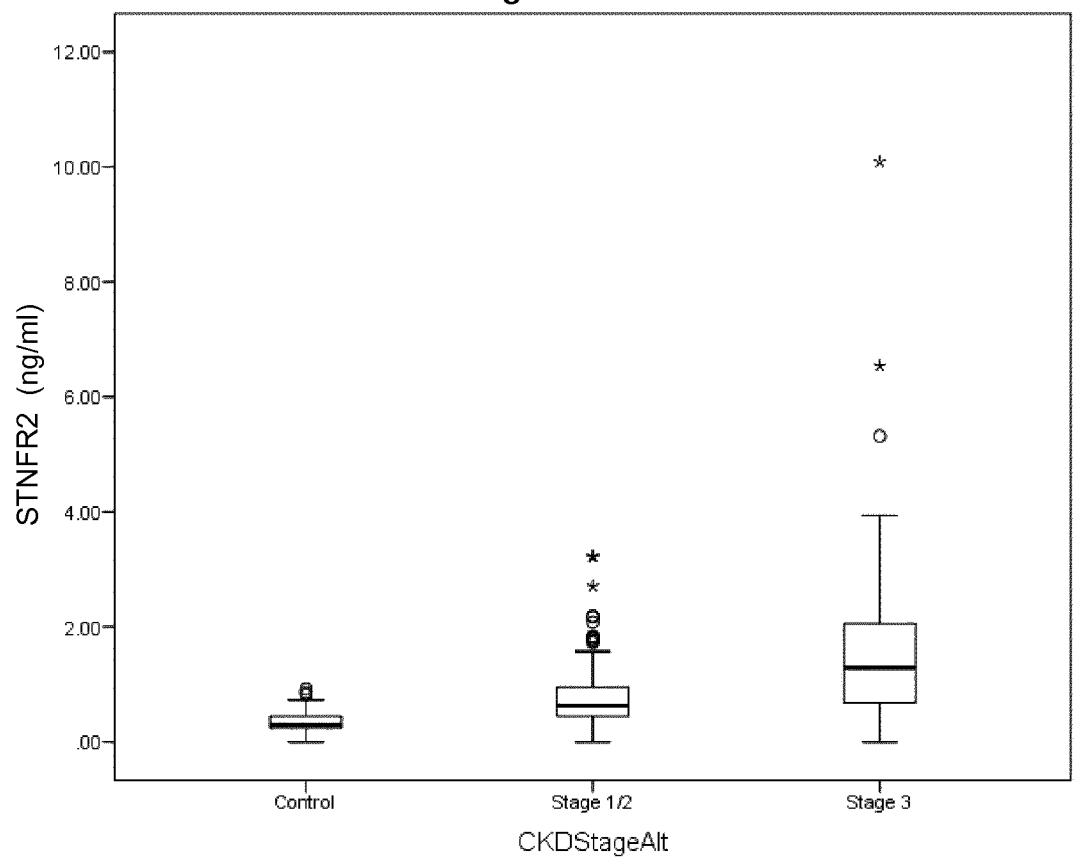
FIG. 4 shows boxplots that summarise the levels of STNFR2, measured in serum samples taken from Healthy controls, patients suffering from Stage 1 or Stage 2 CKD and patients suffering from Stage 3 CKD.
Figure 5:
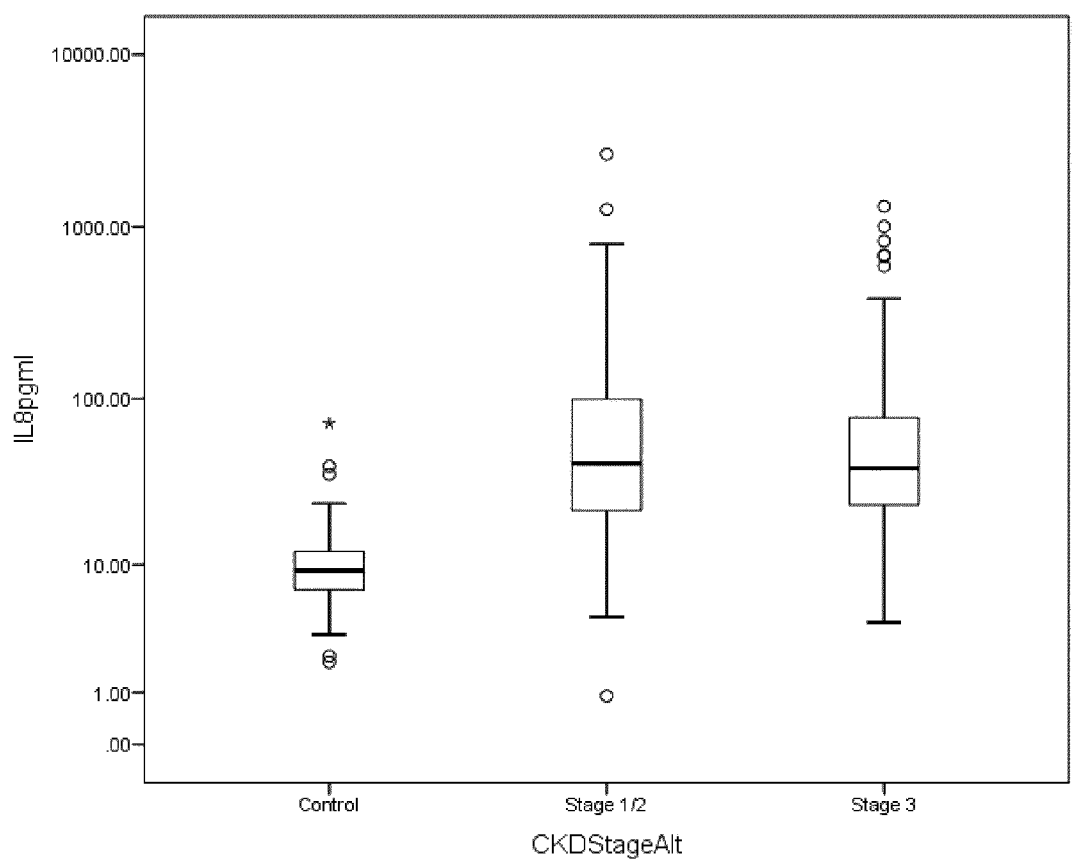
FIG. 5 shows boxplots that summarise the levels of IL-8 measured in serum samples taken from Healthy controls, patients suffering from Stage 1 or Stage 2 CKD and patients suffering from Stage 3 CKD.
Figure 6:
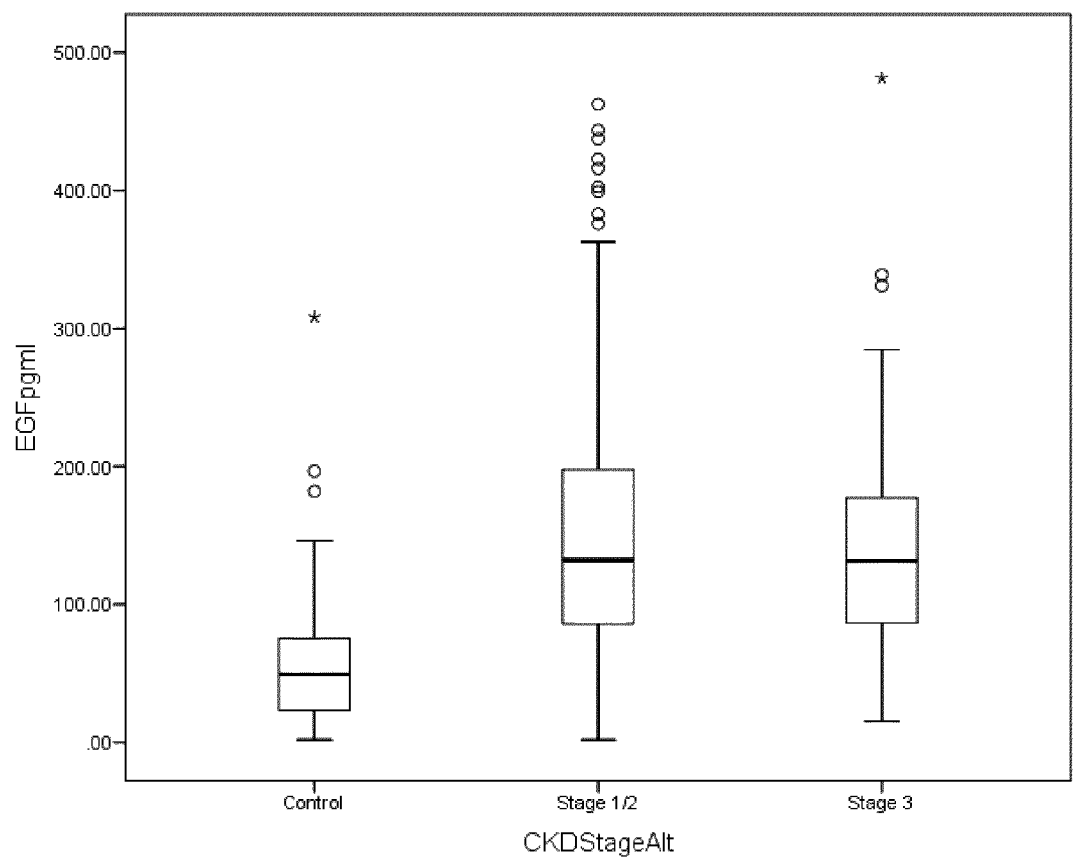
FIG. 6 shows boxplots that summarise the levels of EGF measured in serum samples taken from Healthy controls, patients suffering from Stage 1 or Stage 2 CKD and patients suffering from Stage 3 CKD.
Figure 7:
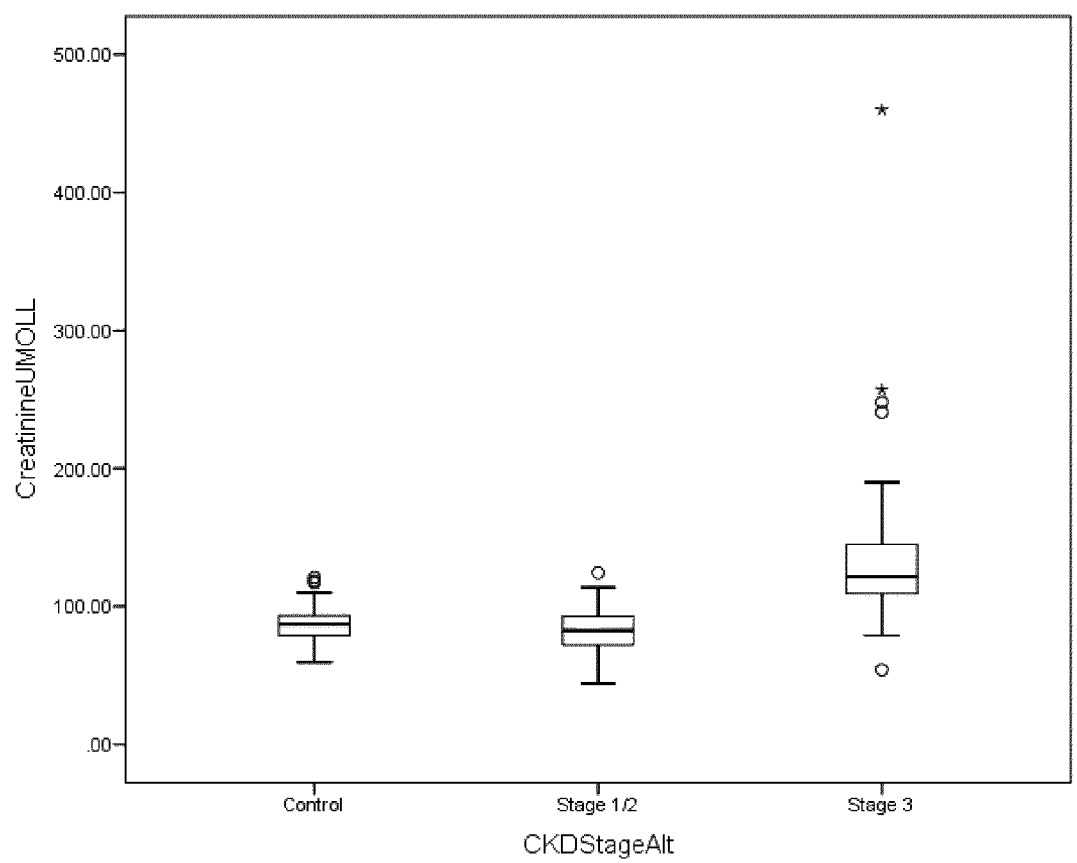
FIG. 7 shows boxplots that summarise the levels of Creatinine measured in serum samples taken from Healthy controls, patients suffering from Stage 1 or Stage 2 CKD and patients suffering from Stage 3 CKD.
Figure 8:
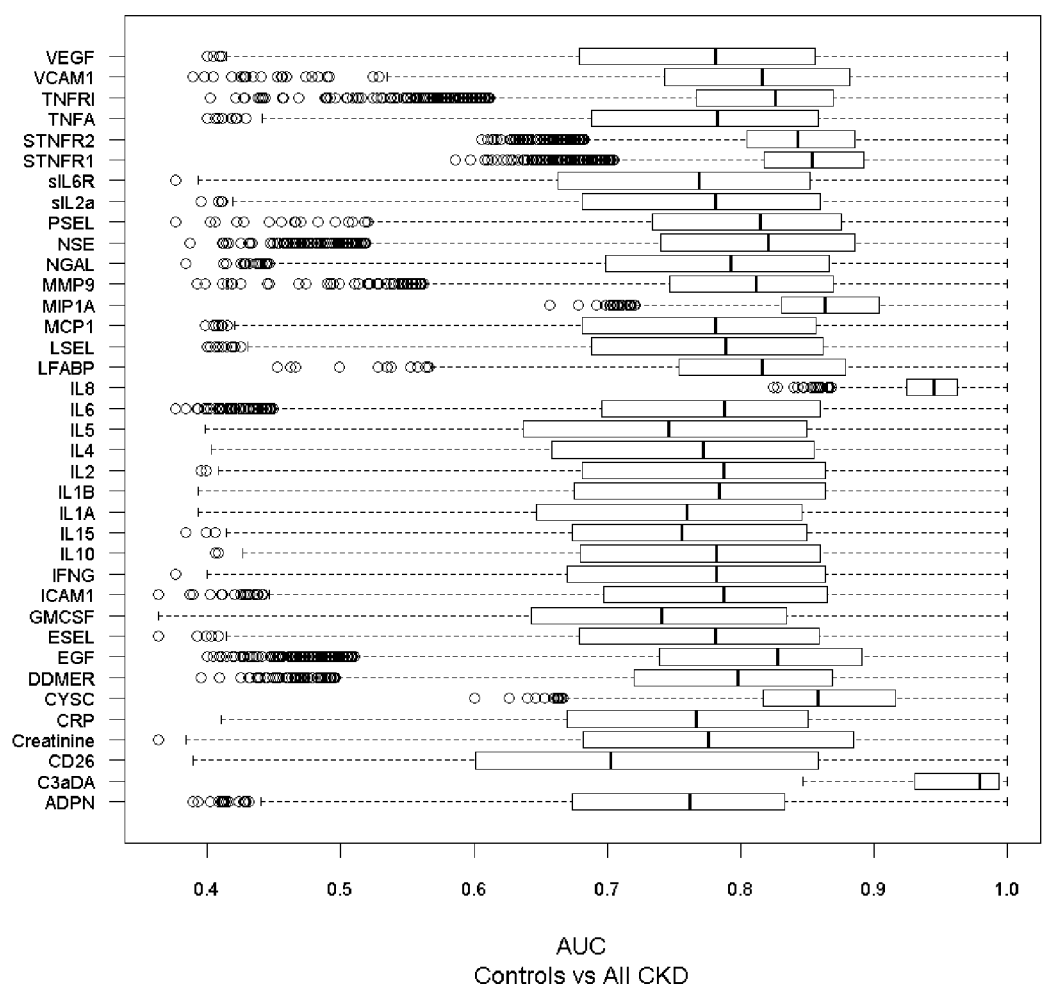
FIG. 8 shows the aggregated AUC values achieved for discriminating control subjects from stage 1, stage 2 and stage 3 chronic kidney disease patients for all combinations that include each biomarker.
Figure 9:
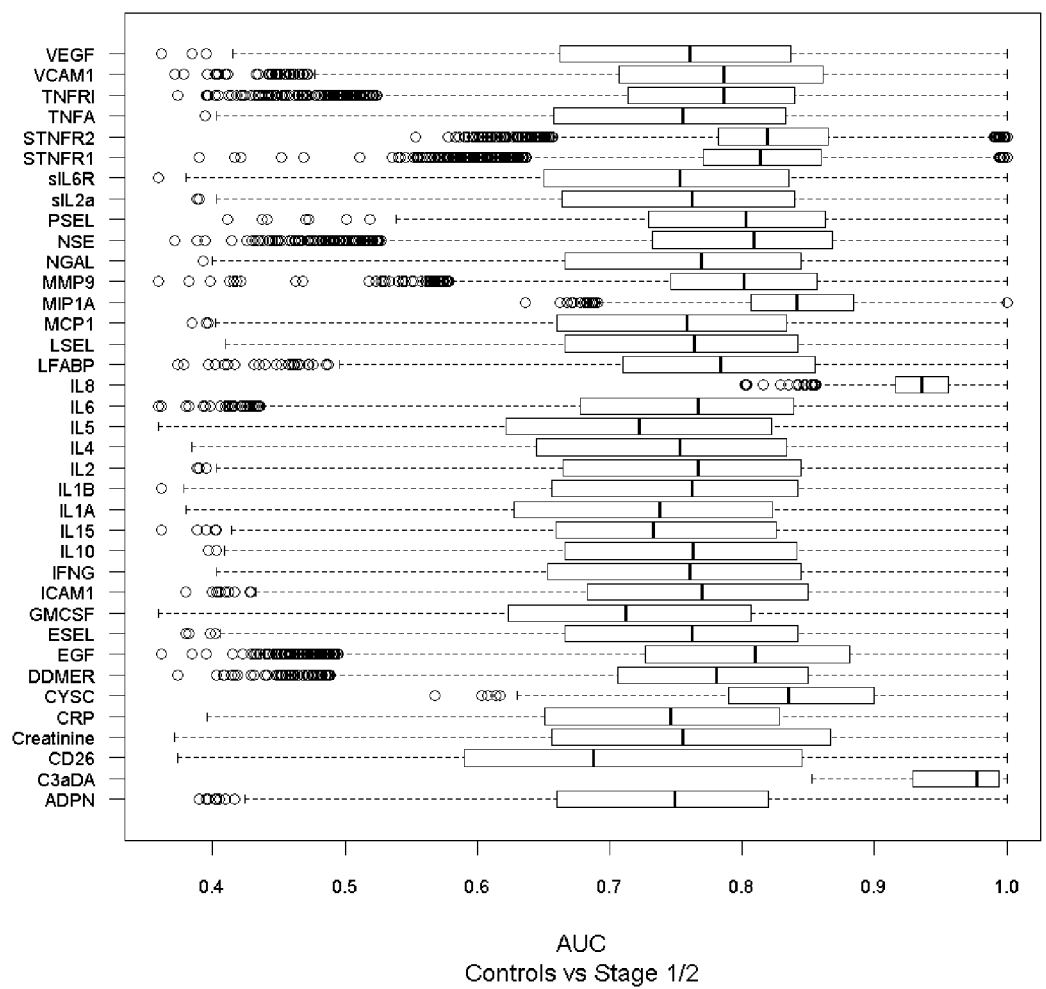
FIG. 9 shows the aggregated AUC values achieved for discriminating stage 1 or stage 2 chronic kidney disease patients from control subjects for all combinations that include each biomarker.
Figure 10:
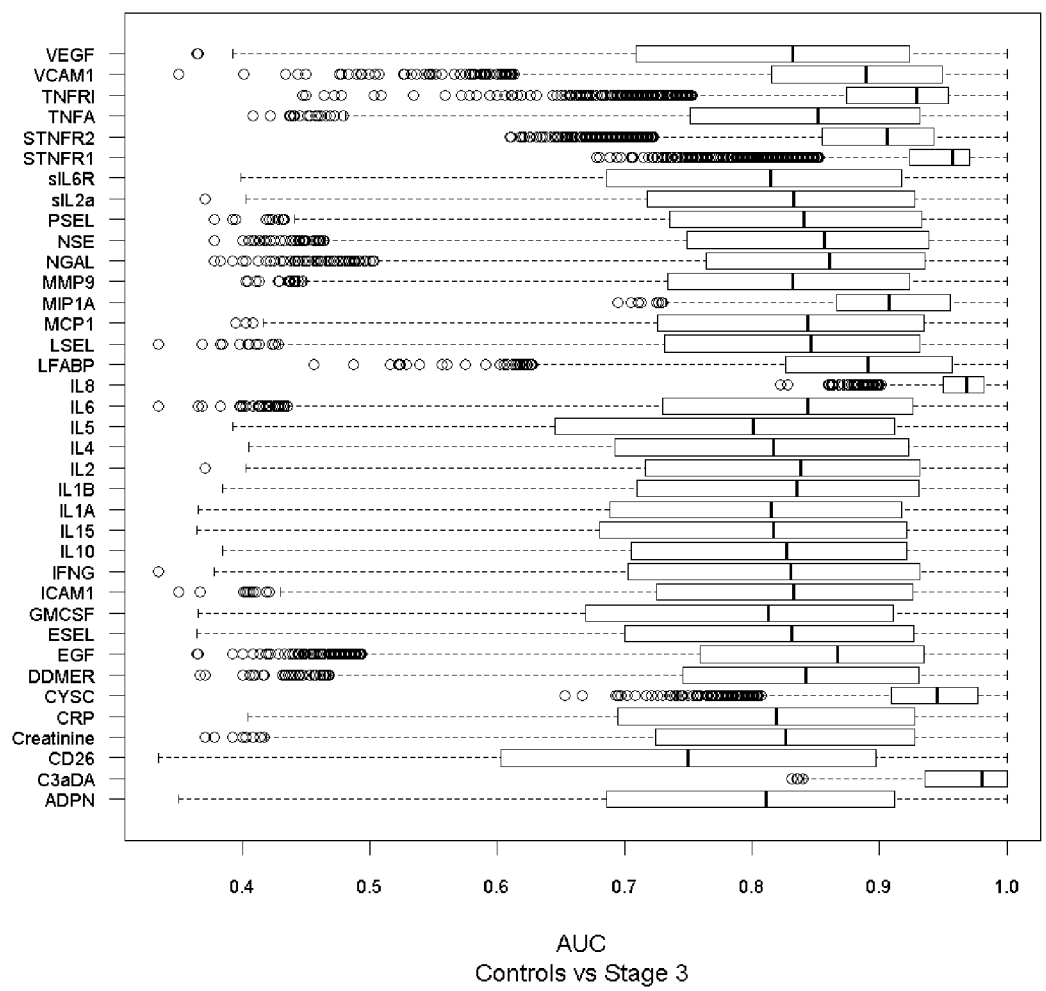
FIG. 10 shows the aggregated AUC values achieved for discriminating stage 3 chronic kidney disease patients from control subjects for all combinations that include each biomarker.
Figure 11:
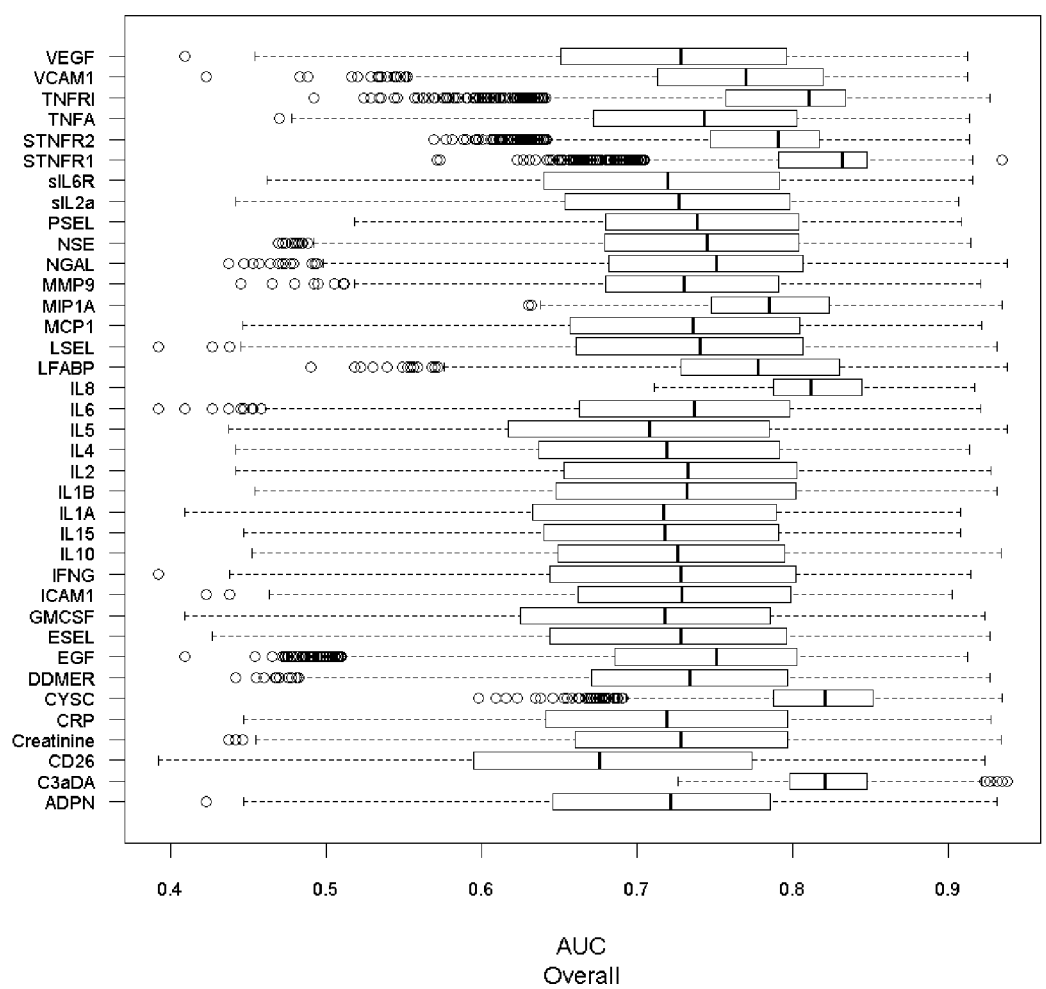
FIG. 11 shows the aggregated AUC values achieved for overall discrimination between all three groups of patients (Control, Stage 1/2, Stage 3) for all combinations that include each biomarker.

The present invention provides a method for the detection of kidney disease by determining the level of a biomarker selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1 in a sample obtained from the patient and comparing the level with a control. An altered level of the biomarker in the sample compared to the control indicates that the patient suffers from, or is at risk of developing, kidney disease.

The term "kidney disease" in the context of the present invention is understood to mean conditions or diseases characterised by a decrease in renal function compared to healthy patients. Kidney disease may include chronic kidney disease (CKD), acute kidney injury (AKI), diabetic nephropathy, glomerulonephritis, focal glomerulosclerosis, immune complex nephropathy or lupus nephritis. Kidney disease may be caused by drug-induced renal injury or kidney graft rejection. Kidney disease may be characterised as nephrotic syndrome or renal insufficiency.

The "amount" of a biomarker refers to the quantity, expression level or concentration of the biomarker within the sample. The amount of a biomarker may also refer to the biomarker measurement expressed as a ratio or percentage of the amount of one or more other analytes. The amount of one or more such other analytes may remain consistent in the majority of samples or conditions. By way of example, the other analytes could be albumin, β-actin or total matrix protein.

The amount of a biomarker may also refer to the biomarker measurement expressed as a ratio or percentage of the amount of one or more other analytes, where the amount of the one or more other analytes is proposed to hold some biochemical significance to the clinical condition of interest.

The term "probe" refers to a molecule that is capable of specifically binding to a target molecule such that the target molecule can be detected as a consequence of said specific binding. Probes that can be used in the present invention include, for example, antibodies, aptamers and oligonucleotides.

The term "antibody" refers to an immunoglobulin which specifically recognises an epitope on a target as determined by the binding characteristics of the immunoglobulin variable domains of the heavy and light chains ($V_H$S and $V_L$S), more specifically the complementarity-determining regions (CDRs). Many potential antibody forms are known in the art, which may include, but are not limited to, a plurality of intact monoclonal antibodies or polyclonal mixtures comprising intact monoclonal antibodies, antibody fragments (for example $F_{ab}$, $F_{ab}$', and $F_v$ fragments, linear antibodies single chain antibodies and multi-specific antibodies comprising antibody fragments), single-chain variable fragments ($scF_v$S), multi-specific antibodies, chimeric antibodies, humanised antibodies and fusion proteins comprising the domains necessary for the recognition of a given epitope on a target. Preferably, references to antibodies in the context of the present invention refer to monoclonal antibodies. Antibodies may also be conjugated to various detectable labels to enable detection, including but not limited to radionuclides, fluorophores, dyes or enzymes including, for example, horse-radish peroxidase and alkaline phosphatase.

The term "aptamer" refers to an oligonucleotide molecule or a polypeptide molecule that specifically binds to a target molecule. Oligonucleotide aptamers may be ribonucleotides (RNA) or deoxyribonucleotides (DNA) and typically consist of short strands of oligonucleotides. Polypeptide aptamers typically consist of short peptide domains that may be attached at one end or at both ends to a protein scaffold.

The term "binds specifically", in the context of antibody-epitope interactions, refers to an interaction wherein the antibody and epitope associate more frequently or rapidly, or with greater duration or affinity, or with any combination of the above, than when either antibody or epitope is substituted for an alternative substance, for example an unrelated protein. Generally, but not necessarily, reference to binding means specific recognition. Furthermore, it is appreciated that an antibody may recognise more than one antigen specifically. Techniques known in the art for determining the specific binding of a target by a monoclonal antibody or lack thereof include but are not limited to, FACS analysis, immunocytochemical staining, immunohistochemistry, western blotting/dot blotting, ELISA, affinity chromatography. By way of example and not limitation, specific binding, or lack thereof, may be determined by comparative analysis with a control comprising the use of an antibody which is known in the art to specifically recognise said target and/or a control comprising the absence of, or minimal, specific recognition of said target (for example wherein the control comprises the use of a non-specific antibody). Said comparative analysis may be either qualitative or quantitative. It is understood, however, that an antibody or binding moiety which demonstrates exclusive specific recognition of a given target is said to have higher specificity for said target when compared with an antibody which, for example, specifically recognises both the target and a homologous protein.

In the context of the present invention, a "control value" is understood to be the level of a particular biomarker, such as C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF or VCAM1 typically found in healthy individuals. The control level of a biomarker may be determined by analysis of a sample isolated from a healthy individual or may be the level of the biomarker understood by the skilled person to be typical for a healthy individual. The "control value" may be a range of values considered by the skilled person to be a normal level for the biomarker in a healthy individual. The skilled person would appreciate that control values for a biomarker may be calculated by the user analysing the level of the biomarker in a sample from a healthy individual or by reference to typical values provided by the manufacturer of the assay used to determine the level of the biomarker in the sample.

Preferably the sample isolated from the patient is a serum sample, but may also be blood, plasma, urine or saliva (particularly with respect to salivary creatinine). The determination of the level of a biomarker may be done on one or more samples from the patient. The sample may be obtained from the patient by methods routinely used in the art.

The present inventors have found that detection of altered levels of a biomarker selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1 in samples can be used to identify patients suffering from CKD or to stage the progression of the disease. Thus, the present invention may be used to diagnose early stage CKD. In the context of the present invention, "early stage" is understood to mean any of the first or second stages of CKD as defined by the KDOQI classification.

In a first aspect, the present invention provides a method of identifying patients suffering from CKD or staging the progression of CKD in a patient comprising measuring the amount of a biomarker in a sample obtained from the subject, and determining whether the amount of the biomarker is altered compared to a normal control, wherein the biomarker is selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1. The control range of values of a biomarker may vary dependent on demographic of population and the sample being tested. For example, the control range of values from a healthy individual may vary from a blood sample compared to a urine sample. The upper and lower threshold for a given sample and patient demographic may be determined by the skilled person by analyzing samples from a patient cohort to find average values. The levels of each biomarker measured in control patients and in patients suffering from CKD are presented in Table 1 below.

In a further aspect, the present invention provides a method of identifying patients at various stages of CKD or staging the progression of CKD comprising measuring the amount of two or more biomarkers in one or more samples obtained from the subject, and determining whether the amount of the biomarkers are altered compared to a normal control, wherein the two or more biomarkers are selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1.

Accuracy of a diagnostic method is best described by its receiver-operating characteristics (ROC) (Zweig, M. H., and Campbell, G., Clin. Chem. 39 (1993) 561-577). The ROC graph is a plot of all of the sensitivity/specificity pairs resulting from continuously varying the decision threshold over the entire range of data observed. A ROC plot depicts the overlap between the two distributions by plotting the sensitivity versus 1–specificity for the complete range of decision thresholds. On the y-axis is sensitivity, or the true-positive fraction defined as [(number of true-positive test results)/(number of true-positive+number of false-negative test results)]. This has also been referred to as positivity in the presence of a disease or condition. It is calculated solely from the affected subgroup. On the x-axis is the false-positive fraction, or 1–specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0 or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always $\geq 0.5$. Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0). In the context of the present invention, Table 2 presents AUC values for individual biomarkers where the altered levels of the biomarkers are used to identify patients suffering from CKD or to stage the progression of CKD.

Where two or more biomarkers are used in the invention, a suitable mathematical or machine learning classification model, such as logistic regression equation, can be derived. The skilled statistician will understand how such a suitable model is derived, which can include other variables such as age and gender of the patient. The ROC curve can be used to assess the accuracy of the model, and the model can be used independently or in an algorithm to aid clinical decision making. Although a logistic regression equation is a common mathematical/statistical procedure used in such cases and an option in the context of the present invention, other mathematical/statistical, decision trees or machine learning procedures can also be used. The skilled person will appreciate that the model generated for a given population may need to be adjusted for application to datasets obtained from different populations or patient cohorts.

The present inventors have further found that detection of altered levels of combinations of two or more biomarkers selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1 can be used to identify patients suffering from CKD or to stage the progression of the disease. In the context of the present invention, Table 3 presents AUC values for combinations of two or more biomarkers where altered levels of the biomarkers are used to identify patients suffering from CKD or to stage the progression of CKD, and where the AUC values for the combination of biomarkers is greater than any single one of the individual biomarkers alone.

In yet a further aspect, the present invention provides a method to support the decision to effect therapeutic intervention in a patient suspected of having renal disease comprising measuring the amount of a biomarker in a sample obtained from the subject, and determining whether the amount of the biomarker is altered compared to a normal control, wherein the biomarker is selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1, and based on the amount of biomarker measured declining or effecting a therapeutic intervention.

The decision to effect a therapeutic intervention will be made by a physician, and said intervention will be designed to combat renal disease. Such therapeutic intervention may include one or more of adult stem cell therapy, transplant therapy, dialysis, diet management, exercise or drug therapy. Drug therapy may be selected from the group consisting of: a diuretic, an angiotensin-converting enzyme inhibitor, angiotensin II receptor antagonist, a beta-adrenergic antagonist, an alpha-adrenergic anatgonist, a calcium channel antagonist, a statin, erythropoietin, vitamin D, vitamin C, vitamin B, folic acid, a hypouricaemic, a phosphate binder, a potassium binding resin, an immunosuppressant and a calcium supplement.

The biomarker measuring step may be replaced by measurement of an immune complex formed on addition to the patient sample of an antibody capable of specifically binding to the biomarker. Binding of the antibody to the biomarker forms an immune complex that can then be detected and measured using standard techniques known in the art.

Table 1 presents the levels of each biomarker measured in serum. For the avoidance of doubt, an increased expression level (when compared to a healthy non-diseased control) of C3a desArg, IL-8, MIP 1α, ADPN, CD26, CRP, CYSC, D-dimer, EGF, ESEL, FABP1, ICAM1, IL10, IL1β, IL5, IL6, MCP1, MMP9, NGAL, PSEL, sIL2α, STNFR1, STNFR2, TNFα, VEGF or VCAM1 indicates the presence of or risk of stage 1 or stage 2 chronic kidney disease. An increased expression level (when compared to a healthy non-diseased control or a stage 1 or stage 2 chronic kidney disease patient) of C3a desArg, IL-8, MIP 1α, ADPN, CD26, Creatinine, CRP, CYSC, D-dimer, EGF, ESEL, FABP1, GMCSF, ICAM1, IL10, IL15, IL1β, IL5, IL6, MCP1, MMP9, NGAL, PSEL, sIL2α, STNFR1, STNFR2, TNFα, VEGF or VCAM1 indicates the presence of or risk of stage 3 chronic kidney disease. A reduced expression level (when compared to a healthy non-diseased control) of Creatinine, IL4, LSEL or NSE indicates the presence of or risk of stage 1 or stage 2 chronic kidney disease. A reduced expression level (when compared to a healthy non-diseased control or a stage 1 or stage 2 chronic kidney disease patient) of IL1α, IL4 or NSE indicates the presence of or risk of stage 3 chronic kidney disease.

Table 2 presents AUC values for individual biomarkers where altered levels of the biomarkers are used to identify patients suffering from CKD or to stage the progression of CKD. The data indicate AUC values for individual biomarker's use to discriminate between healthy control subjects and chronic kidney disease patients (Control v CKD), between healthy control subjects and stage 1 or stage 2 chronic kidney disease patients (Control v Stage 1/2), between healthy control subjects and stage 3 chronic kidney disease patients (Control v Stage 3) and between healthy control subjects, stage 1 or stage 2 chronic kidney disease patients and stage 3 chronic kidney disease patients (Overall).

Table 3 presents AUC values for combinations of two or more biomarkers where altered levels of the biomarkers are used to identify patients suffering from CKD or to stage the progression of CKD. The data indicate AUC values for combinations of biomarkers used to discriminate between healthy control subjects and chronic kidney disease patients (Control v CKD), between healthy control subjects and stage 1 or stage 2 chronic kidney disease patients (Control v Stage 1/2), between healthy control subjects and stage 3 chronic kidney disease patients (Control v Stage 3) and between healthy control subjects, stage 1 or stage 2 chronic kidney disease patients and stage 3 chronic kidney disease patients (Overall).

TABLE 1

Summary of biomarker levels measured in serum

| | | Control | | | Stage 1/2 | | | p vs |
|---|---|---|---|---|---|---|---|---|
| Marker | Units | N | Median | 5-95% | N | Median | 5-95% | Control |
| C3a desARg | ng/ml | 51 | 4458.62 | 1308.8-9540 | 89 | 16525.61 | 6376.3-33913.2 | <0.0001 |
| CD26 | ng/ml | 51 | 821.84 | 466.12-1349.6 | 89 | 996.31 | 495.7-2064.2 | 0.0517 |
| Creatinine | umol/l | 64 | 87.47 | 64.38-115.26 | 89 | 82.66 | 59-108.29 | 0.1219 |
| CRP | mg/LI | 163 | 2.75 | 0.51-13.69 | 294 | 4.61 | 0.59-15.5 | <0.0001 |
| DDMER | ng/ml | 163 | 42.03 | 9.56-97.46 | 295 | 97.03 | 16.42-277.11 | <0.0001 |
| NSE | ng/ml | 163 | 4.94 | 1.89-10.65 | 295 | 2.95 | 0.8-6.27 | <0.0001 |
| NGAL | ng/ml | 163 | 650.34 | 295.13-1089.4 | 295 | 721.52 | 284.09-1373.14 | 0.4302 |
| VCAM1 | ng/ml | 211 | 561.35 | 355.34-851.02 | 273 | 689.46 | 416.89-1050.88 | <0.0001 |
| ICAM1 | ng/ml | 211 | 264.35 | 171.23-381.46 | 273 | 316.55 | 189.78-497.49 | <0.0001 |
| ESEL | ng/ml | 211 | 17.02 | 7.61-31.26 | 273 | 21.72 | 8.14-46.83 | <0.0001 |

TABLE 1-continued

Summary of biomarker levels measured in serum

| Marker | Units | N | Median | 5-95% | N | Median | 5-95% | p |
|---|---|---|---|---|---|---|---|---|
| PSEL | ng/ml | 211 | 165.89 | 96.74-239.44 | 273 | 213.30 | 113.09-322.73 | <0.0001 |
| LSEL | ng/ml | 211 | 1696.57 | 1032.23-2677.06 | 273 | 1660.49 | 978.47-2562.48 | 0.6135 |
| IL5 | pg/ml | 50 | 1.48 | 0.48-4.54 | 98 | 1.84 | 0.47-4.85 | 1.0000 |
| IL15 | pg/ml | 50 | 1.09 | 0.43-1.87 | 102 | 1.02 | 0.53-1.67 | 0.9433 |
| GMCSF | pg/ml | 50 | 1.01 | 0-1.89 | 102 | 1.01 | 0-2.87 | 0.2554 |
| MIP1A | pg/ml | 50 | 5.41 | 3.02-8.23 | 102 | 11.60 | 2.89-29.54 | <0.0001 |
| sIL2a | ng/ml | 163 | 0.17 | 0.08-0.26 | 295 | 0.20 | 0.08-0.38 | 0.0743 |
| sIL6R | ng/ml | 163 | 1.78 | 0.68-3.15 | 295 | 1.72 | 0.54-3.28 | 0.8181 |
| STNFR1 | ng/ml | 163 | 0.44 | 0.23-0.65 | 295 | 0.68 | 0.36-1.16 | <0.0001 |
| STNFR2 | ng/ml | 163 | 0.34 | 0.11-0.67 | 295 | 0.76 | 0.24-1.57 | <0.0001 |
| MMP9 | ng/ml | 163 | 185.88 | 39.34-392.04 | 295 | 341.22 | 76.77-725.82 | <0.0001 |
| IL2 | pg/ml | 164 | 3.03 | 0-6.3 | 295 | 3.00 | 0-9.05 | 1.0000 |
| IL4 | pg/ml | 164 | 3.03 | 1.48-5.36 | 295 | 2.64 | 1.79-3.99 | 1.0000 |
| IL6 | pg/ml | 164 | 2.30 | 0.64-5.21 | 295 | 8.08 | 0.87-11.08 | <0.0001 |
| IL8 | pg/ml | 164 | 10.63 | 4.4-20.83 | 295 | 111.42 | 9.04-510.1 | <0.0001 |
| IL10 | pg/ml | 164 | 1.12 | 0-2.54 | 295 | 3.30 | 0-3.33 | 0.2737 |
| VEGF | pg/ml | 164 | 113.55 | 15.82-266.05 | 295 | 136.23 | 31.04-319.48 | 0.0005 |
| IFNG | pg/ml | 164 | 0.57 | 0.26-1.32 | 295 | 0.58 | 0-1.25 | 0.4417 |
| TNFA | pg/ml | 164 | 2.42 | 1.43-3.41 | 295 | 2.64 | 1.43-4.26 | 0.2495 |
| IL1A | pg/ml | 164 | 0.45 | 0.04-0.56 | 295 | 0.46 | 0.13-0.95 | 1.0000 |
| IL1B | pg/ml | 164 | 1.54 | 0-4.37 | 295 | 2.27 | 0-4.89 | 0.0004 |
| MCP1 | pg/ml | 164 | 234.97 | 80.93-440.1 | 295 | 259.55 | 101.42-533.3 | 0.3432 |
| EGF | pg/ml | 164 | 53.39 | 2.84-115.55 | 295 | 147.39 | 27.7-327.5 | <0.0001 |
| ADPN | ng/ml | 89 | 4372.62 | 812-11022 | 134 | 4949.61 | 955-13746 | 1.0000 |
| CYSC | ng/ml | 89 | 335.02 | 54-707 | 134 | 574.74 | 151.43-1337.3 | <0.0001 |
| FABP1 | ng/ml | 140 | 11.55 | 2.20-27.67 | 112 | 33.20 | 2.07-116.7 | 0.0005 |

| | | | Stage 3 | | | |
|---|---|---|---|---|---|---|
| Marker | Units | N | Median | 5-95% | p vs Control | p vs Stage 1/2 |
| C3a desARg | ng/ml | 44 | 19279.24 | 4539.5-43390 | <0.0001 | 1.0000 |
| CD26 | ng/ml | 44 | 895.60 | 323.05-1765.9 | 1.0000 | 0.5324 |
| Creatinine | umol/l | 44 | 137.87 | 80.5-254.91 | <0.0001 | <0.0001 |
| CRP | mg/LI | 104 | 4.88 | 0.67-14.01 | <0.0001 | 0.9459 |
| DDMER | ng/ml | 105 | 141.95 | 22.52-498.59 | <0.0001 | 0.0021 |
| NSE | ng/ml | 105 | 2.94 | 0.56-9.43 | <0.0001 | 0.2150 |
| NGAL | ng/ml | 105 | 1093.78 | 396.41-1843.17 | <0.0001 | <0.0001 |
| VCAM1 | ng/ml | 105 | 825.37 | 456.68-1507.6 | <0.0001 | 0.0002 |
| ICAM1 | ng/ml | 105 | 341.22 | 175.73-645.56 | <0.0001 | 0.3170 |
| ESEL | ng/ml | 105 | 19.73 | 8.05-37.33 | 0.0174 | 0.7830 |
| PSEL | ng/ml | 105 | 207.42 | 117.7-330.97 | <0.0001 | 1.0000 |
| LSEL | ng/ml | 105 | 1695.86 | 1023.12-2810.2 | 0.0798 | 0.6309 |
| IL5 | pg/ml | 52 | 1.88 | 0.62-8.35 | 1.0000 | 1.0000 |
| IL15 | pg/ml | 52 | 1.30 | 0.52-3.91 | 1.0000 | 0.3000 |
| GMCSF | pg/ml | 52 | 1.24 | 0-6.12 | 0.9645 | 1.0000 |
| MIP1A | pg/ml | 52 | 15.59 | 4.01-34.34 | <0.0001 | 0.1575 |
| sIL2a | ng/ml | 105 | 0.26 | 0.07-0.5 | <0.0001 | 0.0002 |
| sIL6R | ng/ml | 105 | 2.07 | 0.89-3.93 | 0.0854 | 0.0015 |
| STNFR1 | ng/ml | 105 | 1.27 | 0.59-2.69 | <0.0001 | <0.0001 |
| STNFR2 | ng/ml | 105 | 1.58 | 0.28-3.71 | <0.0001 | <0.0001 |
| MMP9 | ng/ml | 105 | 320.99 | 54.05-734.84 | <0.0001 | 1.0000 |
| IL2 | pg/ml | 105 | 3.06 | 0-6.02 | 0.3807 | 1.0000 |
| IL4 | pg/ml | 105 | 2.53 | 1.66-3.95 | 0.3568 | 0.0210 |
| IL6 | pg/ml | 105 | 8.93 | 1.3-21.38 | <0.0001 | <0.0001 |
| IL8 | pg/ml | 105 | 108.26 | 11.96-650.72 | <0.0001 | 1.0000 |
| IL10 | pg/ml | 105 | 1.51 | 0-3.62 | 0.2761 | 1.0000 |
| VEGF | pg/ml | 105 | 122.89 | 37.53-271.83 | 0.0245 | 1.0000 |
| IFNG | pg/ml | 105 | 0.57 | 0-1.9 | 1.0000 | 1.0000 |
| TNFA | pg/ml | 105 | 3.47 | 1.98-5.28 | <0.0001 | <0.0001 |
| IL1A | pg/ml | 105 | 0.31 | 0-0.73 | 1.0000 | 0.8398 |
| IL1B | pg/ml | 105 | 1.87 | 0-3.9 | 0.2326 | 0.3362 |
| MCP1 | pg/ml | 105 | 276.85 | 112.64-528.43 | 0.0178 | 0.2368 |
| EGF | pg/ml | 105 | 139.33 | 27.92-281.65 | <0.0001 | 1.0000 |
| ADPN | ng/ml | 24 | 9472.29 | 1603.67-43539.5 | 0.0037 | 0.0070 |
| CYSC | ng/ml | 24 | 1244.60 | 467.25-4081.62 | <0.0001 | <0.0001 |
| FABP1 | ng/ml | 44 | 80.53 | 4.53-322.65 | 0.0001 | 0.0061 |

TABLE 2

AUC values calculated for altered levels of individual biomarkers in diagnosis and staging of CKD

| Biomarker | Control vs CKD | Control Vs Stage 1/2 | Control Vs Stage 3 | Overall |
|---|---|---|---|---|
| C3aDA | 0.96 | 0.976 | 0.932 | 0.817 |
| CD26 | 0.583 | 0.634 | 0.496 | 0.585 |
| Creatinine | 0.613 | 0.57 | 0.926 | 0.81 |
| CRP | 0.643 | 0.622 | 0.701 | 0.636 |
| DDMER | 0.763 | 0.738 | 0.828 | 0.734 |
| NSE | 0.725 | 0.715 | 0.752 | 0.682 |
| NGAL | 0.636 | 0.56 | 0.839 | 0.726 |
| VCAM1 | 0.697 | 0.659 | 0.788 | 0.697 |
| ICAM1 | 0.664 | 0.645 | 0.711 | 0.65 |
| ESEL | 0.595 | 0.602 | 0.578 | 0.568 |
| PSEL | 0.694 | 0.697 | 0.687 | 0.628 |
| LSEL | 0.583 | 0.58 | 0.588 | 0.556 |
| IL5 | 0.497 | 0.496 | 0.499 | 0.497 |
| IL15 | 0.508 | 0.553 | 0.633 | 0.631 |
| GMCSF | 0.532 | 0.578 | 0.562 | 0.588 |
| IL2 | 0.495 | 0.498 | 0.486 | 0.491 |
| IL4 | 0.488 | 0.474 | 0.526 | 0.52 |
| IL6 | 0.765 | 0.731 | 0.853 | 0.747 |
| IL8 | 0.929 | 0.925 | 0.939 | 0.79 |
| IL10 | 0.589 | 0.57 | 0.637 | 0.586 |
| VEGF | 0.596 | 0.594 | 0.602 | 0.565 |
| IFNG | 0.533 | 0.539 | 0.515 | 0.526 |
| TNFA | 0.605 | 0.534 | 0.793 | 0.685 |
| IL1A | 0.479 | 0.487 | 0.458 | 0.488 |
| IL1B | 0.631 | 0.626 | 0.645 | 0.587 |
| MCP1 | 0.571 | 0.563 | 0.593 | 0.564 |
| EGF | 0.868 | 0.87 | 0.865 | 0.742 |
| ADPN | 0.52 | 0.547 | 0.647 | 0.621 |
| CYSC | 0.727 | 0.691 | 0.947 | 0.827 |
| FABP1 | 0.655 | 0.624 | 0.734 | / |
| MIP1A | 0.86 | 0.836 | 0.91 | 0.802 |
| sIL2a | 0.59 | 0.53 | 0.749 | 0.657 |
| sIL6R | 0.521 | 0.544 | 0.541 | 0.559 |
| STNFR1 | 0.863 | 0.815 | 0.989 | 0.886 |
| STNFR2 | 0.866 | 0.841 | 0.931 | 0.843 |
| MMP9 | 0.747 | 0.745 | 0.752 | 0.674 |

TABLE 3

AUC values calculated for altered levels of combinations of two or more biomarkers in diagnosis and staging of CKD.

| | Control vs CKD | Control Vs Stage 1/2 | Control Vs Stage 3 | Overall | Number |
|---|---|---|---|---|---|
| C3aDA, CYSC, CRP | 0.985 | 0.979 | 1 | 0.859 | 106 |
| C3aDA, GMCSF | 0.992 | 0.992 | 0.992 | 0.84 | 108 |
| C3aDA, IL5 | 0.992 | 0.991 | 0.995 | 0.84 | 104 |
| C3aDA, MIP1A | 0.998 | 1 | 0.995 | 0.833 | 108 |
| C3aDA, GMCSF, CYSC | 1 | 1 | 1 | 0.884 | 97 |
| C3aDA, PSEL, GMCSF | 1 | 1 | 1 | 0.878 | 108 |
| C3aDA, PSEL, IL5 | 0.988 | 0.985 | 0.995 | 0.906 | 104 |
| C3aDA, MIP1A, CYSC | 1 | 1 | 1 | 0.873 | 97 |
| C3aDA, GMCSF, IL6 | 0.994 | 0.995 | 0.992 | 0.89 | 108 |
| C3aDA, ESEL, MIP1A | 1 | 1 | 1 | 0.865 | 108 |
| C3aDA, GMCSF, IL4 | 0.995 | 0.995 | 0.995 | 0.879 | 108 |
| C3aDA, Creatinine, IL2 | 0.994 | 0.991 | 1 | 0.877 | 159 |
| C3aDA, NGAL, PSEL, IL5 | 0.999 | 1 | 0.997 | 0.912 | 104 |
| C3aDA, NGAL, PSEL, GMCSF | 1 | 1 | 1 | 0.899 | 108 |
| C3aDA, GMCSF, MIP1A, CYSC | 1 | 1 | 1 | 0.897 | 97 |
| C3aDA, IL5, IFNG, CYSC | 1 | 1 | 1 | 0.892 | 93 |
| C3aDA, DDMER, IL5, CYSC | 1 | 1 | 1 | 0.891 | 93 |
| C3aDA, NGAL, PSEL, IL15 | 0.993 | 0.992 | 0.995 | 0.911 | 108 |
| C3aDA, MIP1A, TNFA, CYSC | 1 | 1 | 1 | 0.889 | 97 |
| C3aDA, ICAM1, IL5, IL1A | 0.987 | 0.981 | 1 | 0.921 | 104 |
| MIP1A, IL8, IL1B, CYSC | 0.995 | 0.994 | 1 | 0.89 | 121 |
| VCAM1, IL15, IL8, CYSC | 1 | 1 | 1 | 0.862 | 121 |
| VCAM1, MIP1A, IL8, CYSC | 1 | 1 | 1 | 0.861 | 121 |
| NSE, MIP1A, IL8, CYSC | 1 | 1 | 1 | 0.807 | 121 |
| NSE, VCAM1, MIP1A, IL8 | 0.999 | 1 | 0.999 | 0.87 | 191 |
| FABP1, IL8, MIP1A, DDMER | 0.985 | 0.978 | 1 | 0.831 | 114 |
| FABP1, IL8, MIP1A, NGAL | 0.991 | 0.986 | 1 | 0.822 | 114 |
| FABP1, IL8, MIP1A, EGF | 0.977 | 0.969 | 0.996 | 0.818 | 114 |

The stratification of patients into one of the stages of CKD is useful to assess whether a patient would benefit from one treatment type compared to another and also to monitor whether a treatment is successful. Stratification of patients also assists in determining the prognosis of the patient thereby enabling future care requirements.

The methods of the present invention may use methods for determining the level of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 known in the art, such as enzymatic and/or chemical protein determination or immunological assay based methods. Immunological assays for determining the level of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 can be performed in a variety of assay formats, including sandwich assays e.g. (ELISA), competition assays (competitive RIA), bridge immunoassays, immunohistochemistry (IHC) and immunocytochemistry (ICC). Methods for determining the level of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 include contacting a patient sample with antibodies that bind to C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 and detecting binding. Antibodies having specificity for C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 can be immobilised on a support material using conventional methods. Binding of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 to the antibodies on the support can be detected using further antibodies having specificity or reactivity (which may be for the biomarker or other discriminating analyte) for C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 or by using physical methods such as surface plasmon resonance (Biacore Int, Sweden).

Preferably, a solid state device may be used to determine the level of one or more biomarkers selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 in the sample isolated from the patient. The solid state device comprises a substrate having an activated surface on to which is applied an antibody to C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 to discreet areas of the activated surface. Preferably the solid state device may perform multi-analyte assays such that the level of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 in a sample isolated from the patient may be determined simultaneously with the level of any others of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 in the sample. In this embodiment, the solid state device has a multiplicity of discrete reaction sites each bearing a desired antibody covalently bound to the substrate, and in which the surface of the substrate between the reaction sites is inert with respect to the target biomarker. The solid state, multi-analyte device used in the present invention may therefore exhibit little or no non-specific binding.

A device that may be used in the invention may be prepared by activating the surface of a suitable substrate, and applying an array of antibodies on to discrete sites on the surface. Suitable substrates are produced from any inert materials such as plastics, ceramics or glass. If desired, the other active areas may be blocked. The ligands may be bound to the substrate via a linker, e.g. by covalent attachment. In particular, it is preferred that the activated surface is reacted successively with an organosilane, a bifunctional linker and the antibody. The solid state device used in the methods of the present invention may be manufactured according to the method disclosed in, for example, GB-A-2324866 the contents of which is incorporated herein in its entirety. Preferably, the solid state device used in the methods of the present invention is a biochip which forms part of the Biochip Array Technology system (BAT) (available from Randox Laboratories Limited).

The solid state device used in the method of the present invention comprises an antibody to C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1. Preferably the antibody is specific for C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 and exhibits a cross-reactivity of less than 0.5%, preferably less than 0.1%, to other antigens. Preferably, the antibody is a monoclonal antibody. The solid state device used in the method of the present invention can be processed employing BAT analysers from Randox.

The present invention further provides assays to measure the amount of two or more biomarkers in a sample obtained from the subject, wherein the biomarkers are selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LSEL, MCP1, MMP9, NGAL, NSE, PSEL, sIL2α, sIL6R, STNFR1, STNFR2, TNFα, VEGF and VCAM1. The assays of the invention can be used to measure the levels of combinations of three, four, five, six, seven or more of these biomarkers in a sample. Such assays can be carried out using the solid state devices of the invention, and they may be used in the methods of the invention.

The methods of the present invention may be used to monitor a patient post-operatively to assess the risk of them developing renal complications. Specifically, a sample may be obtained from a patient at given intervals post operatively and the level of any one or more biomarkers selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 in the sample determined. An assessment of the level of any one or more biomarkers selected from the group consisting of C3a desArg, IL-8, MIP 1α, ADPN, CD26, Creatinine, CRP, CYSC, D-dimer, EGF, ESEL, FABP1, GMCSF, ICAM1, IFNγ, IL10, IL15, IL1α, IL1β, IL2, IL4, IL5, IL6, LFABP, LSEL, MCP1, MMP9, NGAL, NSE, PSEL, sIL2α, sIL6R, STNFR1, STNFR2, TNFα, VEGF or VCAM1 over a particular time frame provides the clinician with an indication of whether the patient is suffering early stage CKD and medical intervention can be taken accordingly.

EXAMPLE

Serum samples from 376 patients suffering from chronic kidney disease and 211 healthy controls were taken by means of venepuncture in a method known in the art and stored at −80° C. until ready for use. Patients' CKD was staged using the KDOQI guidelines, and patients suffering from Stage 1 and Stage 2 CKD were combined for the purpose of this analysis as being representative of early kidney disease that is not easily determined through conventional biomarker-based methods.

The sample cohort was composed of:
587 serum samples in total
271 CKD stage 1/2 patients
105 CKD stage 3 patients
211 donor controls In order to determine the levels of biomarkers in the sample, immunoassays using the biochip array technology (BAT) were employed, with the exception of creatinine measurement. Creatinine was measured using a commercially available clinical chemistry assay (Product number CR3814; Randox Laboratories), and samples were analysed on the RX Daytona (available from Randox Laboratories).
Protocol Description Data were reported in the respective units of the assay and no normalisation techniques were used prior to analysis. Data were first analysed through conventional univariant non-parametric testing. Table 1 reports the median and 5 to 95 percentile of each analyte studied. Significance was determined using mann-whitney with bonferroni correction for multiple comparisons (Control vs Stage 1/2, Control vs Stage 3, Stage 1/2 vs Stage 3). Receiver-operator characteristics (ROC) analysis was also performed on this data and the area under the curve determined for the identification of; all CKD patients (Stage 1/2/3) versus healthy controls, Stage 1/2 versus healthy controls, Stage 3 versus healthy controls and for differentiating between healthy controls, Stage 1/2 and Stage 3 (Overall). These AUC values have been summarised in table 2.

In order to determine whether potential combinations of markers may have improved diagnostic and stratification performance, two methods were employed. The first was the use of logistic regression, where a subset of the cohort was used to develop a model for distinguishing CKD patients from healthy controls. Backward entry was used to select the optimal variables required. This model was then validated on a validation subset, the predicted probability of CKD was calculated using the logistic regression equation and then ROC analysis was performed.

The second method was carried out to fully examine the value in combining these biomarkers to improve diagnostic performance and disease stratification, random forests were grown using a randomly selected subset of the data for all possible single, double, triple and quadruple biomarker combinations. In total 66,675 models were generated and the AUC was calculated from a separate validation subset. The AUCs for all the combinations that contain each value were aggregated and those markers whose average aggregated AUC were highest were deemed to be the most important markers. In this C3a desArg was shown to perform best in almost any combination and was present in 78% of the top performing models. Table 3 represent the AUCs of some combinations in discriminating CKD and differentiating the stage of disease.

The invention claimed is:

1. A method for detecting kidney disease, comprising
obtaining a serum, blood or plasma sample from a subject;
contacting the serum, blood or plasma sample with a solid support having immobilized thereon a plurality of antibodies that specifically bind to the biomarkers complement C3a (des) Arg (C3a desArg), macrophage inflammatory protein 1 alpha (MIP1α) and optionally any of the biomarkers selected from group (a) or group (b) consisting of:
(a) Interleukin-8 (IL-8), adiponectin (ADPN), dipeptidyl peptidase 4 (CD26), c-reactive protein (CRP), cystatin c (CYSC), D-dimer, endothelial growth factor (EGF), e-selectin (ESEL), granulocyte-macrophage colony stimulating factor (GMCSF), intercellular adhesion molecule 1 (ICAM1), interferon gamma (IFNγ), interleukin 10 (IL10), interleukin 15 (IL15), interleukin 1β(IL1β), interleukin 5 (IL5), interleukin 6 (IL6), liver fatty acid binding protein (LFABP), monocyte chemotactic protein 1 (MCP1), matrix metalloproteinase 9 (MMP9), neutrophil gelatinase-associated lipocalin (NGAL), p selectin (PSEL), soluble interleukin 2 alpha (sIL2α), soluble tumour necrosis factor receptor 2 (STNFR2), soluble tumour necrosis factor 1 (STNFR1), tumour necrosis factor alpha (TNFα), vascular endothelial growth factor (VEGF), vascular cell adhesion molecule 1 (VCAM1), and any combination thereof;
(b) creatinine, interleukin-4 (IL4), L-selectin (LSEL), neuron specific enolase (NSE), interleukin 1α (IL1α), and
measuring the binding of said biomarkers to the antibodies on the solid support, wherein if C3a desArg and MIP1α are increased in the sample with respect to a normal control value, and optionally whether one or more biomarker from group (a) are increased and one or more biomarkers from group (b) are decreased with respect to a normal control value is indicative of kidney disease.

2. A method according to claim 1, wherein the kidney disease is stage 1, stage 2 or stage 3 chronic kidney disease.

3. A method according to claim 1, wherein the sample is plasma or serum.

4. A method according to claim 1, wherein the plurality of antibodies are detectably-labelled.

5. A method according to claim 4, wherein the detectable label is horse-radish peroxidase.

6. A method according to claim 1, wherein the solid support is a biochip.

7. A method according to claim 6, wherein the amount of a biomarker in the sample is measured using a sandwich ELISA assay.

8. A method according to claim 1, wherein the levels of C3a desArg, CYSC and MIP1α are measured.

9. A method according to claim 1, wherein the levels of C3a desArg, GMCSF, CYSC and MIP1α are measured.

10. A method according to claim 1, wherein the levels of C3a desArg, TNFA, CYSC and MIP1α are measured.

11. A method according to claim 1, wherein the levels of C3a desArg, CRP, CYSC, EGF, FABP1, IL8, sTNFR1, sTNFR2, D-dimer, NGAL and MIP1α are measured.

* * * * *